US012446704B2

(12) United States Patent
Wu

(10) Patent No.: US 12,446,704 B2
(45) Date of Patent: Oct. 21, 2025

(54) ELECTRIC ROCKING BED

(71) Applicant: Peter Wu, Arlington, TX (US)

(72) Inventor: Peter Wu, Arlington, TX (US)

( * ) Notice: Subject to any disclaimer, the term of this patent is extended or adjusted under 35 U.S.C. 154(b) by 244 days.

(21) Appl. No.: 17/886,879

(22) Filed: Aug. 12, 2022

(65) Prior Publication Data

US 2024/0049888 A1 Feb. 15, 2024

(51) Int. Cl.

| | |
|---|---|
| ***A47C 21/00*** | (2006.01) |
| ***A61H 1/00*** | (2006.01) |
| ***A61M 21/02*** | (2006.01) |
| *A61M 21/00* | (2006.01) |

(52) U.S. Cl.

CPC ........... *A47C 21/006* (2013.01); *A61H 1/005* (2013.01); *A61M 21/02* (2013.01); *A61H 2201/0142* (2013.01); *A61H 2201/1215* (2013.01); *A61H 2201/149* (2013.01); *A61H 2201/1676* (2013.01); *A61M 2021/0022* (2013.01)

(58) Field of Classification Search

CPC ...... A47C 21/00; A47C 21/006; A61H 1/005; A61H 2201/0142; A61H 2201/1215; A61H 2201/149; A61H 2201/1676

See application file for complete search history.

(56) References Cited

U.S. PATENT DOCUMENTS

| | | | | |
|---|---|---|---|---|
| 4,274,167 | A * | 6/1981 | Immel | A61G 7/00 5/915 |
| 4,277,857 | A * | 7/1981 | Svehaug | A47C 21/006 5/108 |
| 8,707,477 | B1 * | 4/2014 | Flemister | A47C 21/006 5/108 |
| 8,789,220 | B2 | 7/2014 | Flemister | |
| 2008/0000026 | A1 * | 1/2008 | Sims, Jr. | A47C 21/006 5/607 |
| 2010/0325794 | A1 * | 12/2010 | Chung | A47C 21/006 5/103 |
| 2013/0007958 | A1 * | 1/2013 | Flemister | A61G 7/005 5/609 |

* cited by examiner

*Primary Examiner* — Fredrick C Conley
(74) *Attorney, Agent, or Firm* — Jackson Walker LLP

(57) ABSTRACT

An electric rocking bed is described which comprises a base and a bed frame arranged on the base, and is characterized in that the bottom of the bed frame is movably connected to the base through a number of swing parts. The base is provided with at least one drive part that drives the action of the bed frame. When the drive part is working, the swing part drives the bed frame to swing from head to tail. The beneficial effect of the utility model is that the utility model has a simple structure, only needs a driving part to drive the work, and drives the bed frame to a rocking movement through the swinging part. The swinging process is stable and silent, which is conducive to a fast and deep sleep.

9 Claims, 8 Drawing Sheets

ELECTRIC ROCKING BED

BACKGROUND

This disclosure relates to the technical field of electric beds, in particular to an electric rocking bed.

Nowadays, there are many kinds of electric beds, and the parts of the conventional electric bed frame are relatively fixed. In order to improve the comfort and help people to fall asleep easily, it is necessary to improve the electric bed, especially to redesign the bed frame, so that the bed frame may rock from head to tail at a comfortable range. In addition, although there are also rocking electric beds at present market, their structural setting is unreasonable. The position of the support point is set at the central point of the bed. In fact, the position that people lay on the bed is not fixed. People also turn over and move during sleep. When the gravity of the human body deviates from the central point of the bed, the load of the motor and the operation of the machinery will change simultaneously, and such load difference results in the noise and friction sound of the motor and mechanical parts. Therefore, what is needed is an electric rocking bed with a more stable structure, which can contribute to a fast deep sleep and alleviate mechanical noise as well.

SUMMARY

The present disclosure relates generally to an electric rocking bed.

The purpose of this disclosure is to provide a new type of electric rocking bed to solve the above-mentioned problems with available designs.

The technical problems solved by the current bed design are accomplished as follows.

An electric rocking bed includes a base and a bed frame sit on the base, which is characterized in that the bottom of the bed frame is movably connected to the base through a number of swing parts, and at least one drive part is arranged on the base to drive the bed frame action. When the drive part is in action, it drives the bed frame to rock from head to tail through the swing part.

In a preferred embodiment of the electric rocking bed, the swing part comprises a support frame, a bed frame strut and a swing arm. One end of the bed frame strut is fixed at the bottom of the bed frame, and the other end is rotationally connected with one end of the swing arm. The other end of the swing arm is rotationally connected to the support frame.

In a further preferred embodiment of the electric rocking bed, both sides of the middle part of the base are respectively provided with the swing parts.

In a further preferred embodiment of the electric rocking bed, both sides of each support frame are respectively provided with a swing arm, and the bottom of the bed frame on the side corresponding to the support frame is provided with two bed frame struts corresponding to the two swing arms on the side.

In a further preferred embodiment of the electric rocking bed, the driving component includes a rotating motor fixed on the base, the output end of the rotating motor is connected with one end of a reducer, the other end of the reducer is connected with the transmission gear, the base is provided with a rotating shaft, the rotating shaft is provided with a driven gear connected with the transmission gear through a synchronous belt, and the rotating shaft is connected with one end of the first rotating arm, The other end of the first rotating arm is rotationally connected with one end of the second rotating arm, and the other end of the second rotating arm is rotationally connected with the bed frame.

In a further preferred embodiment of the electric rocking bed, both ends of the rotating shaft are respectively connected with the bearing assembly on the base, and one end of the rotating shaft extends out of the bearing assembly and is connected with one end of the first rotating arm.

In a further preferred embodiment of the electric rocking bed, the base is provided with a motor mounting base.

The benefits of the current described electric rocking bed are as follows: the electric rocking bed has a simple structure, only one driving part is needed, and the bed frame is driven to rock from head to tail through the swing part. The swing process is stable and quiet, which is conducive to a fast and deep sleep. In addition, the electric rocking bed further sets the fulcrum of the bed on both sides on the middle of the base, makes the thrust of rocking average through the specially designed driving parts, which reduces the impact on the motor and mechanical parts due to the posture change of the human body on the bed, and alleviates the noise of the motor and mechanical parts due to the change of load.

BRIEF DESCRIPTION OF THE DRAWINGS

In order to more clearly explain the embodiments of the electric rocking bed described herein or its associated technical solutions, the attached drawings described below will be used in the description. The drawings discussed in the following description are only some embodiments of the electric rocking bed. Those skilled in the art will recognize that further preferred embodiments exist that are not explicitly illustrated in these drawings.

DETAILED DESCRIPTION OF PREFERRED EMBODIMENTS

The present disclosure relates to an electric rocking bed.

In order to better describe the technical and creative features, purpose and efficacy of the electric rocking bed, the electric rocking bed is further described below with reference to preferred embodiments and associated drawings.

Figure 1:
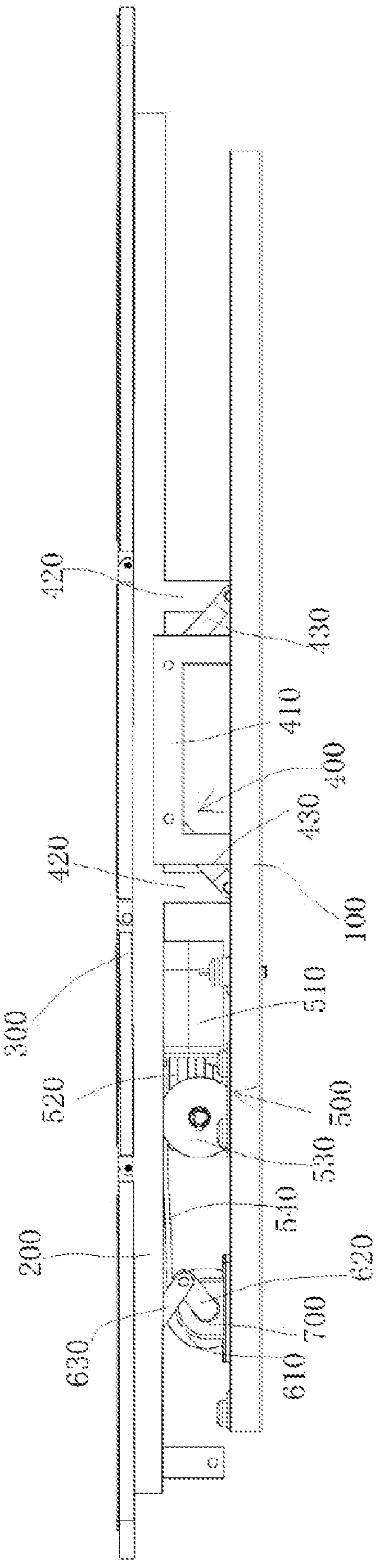
FIG. 1 shows a side view of an exemplary electric rocking bed in accordance with preferred embodiments described herein.

A preferred embodiment of an electric rocking bed shown in FIG. 1 includes a base 100 and a bed frame 200 arranged on the base 100. The bed frame 200 in this embodiment is provided with a bed surface 300. The bed surface 300 can be fixedly connected with the bed frame 200 or detachably connected with the bed frame 200. In order to facilitate transportation, the bed surface 300 can be set as a folding bed frame. The structure of the bed surface 300 may be formed by splicing a plurality of plates, with the adjacent two bed plates being connected by turn pins. Its connection mode can be fixed on the bed frame 200 by screws or may be detachably connected with the bed frame 200 by adopting a buckle structure.

In the preferred embodiment shown in FIG. 1, the bottom of the bed frame 200 is movably connected to the base 100 through a number of swinging parts 400, and at least one driving part 500 driving the action of the bed frame 200 is arranged on the base 100. When the driving part 500 is engaged, the swinging part 400 drives the bed frame 200 to swing from head to tail, thereby driving the bed surface 300 connected with the bed frame 200 to a rocking movement.

Figure 4:
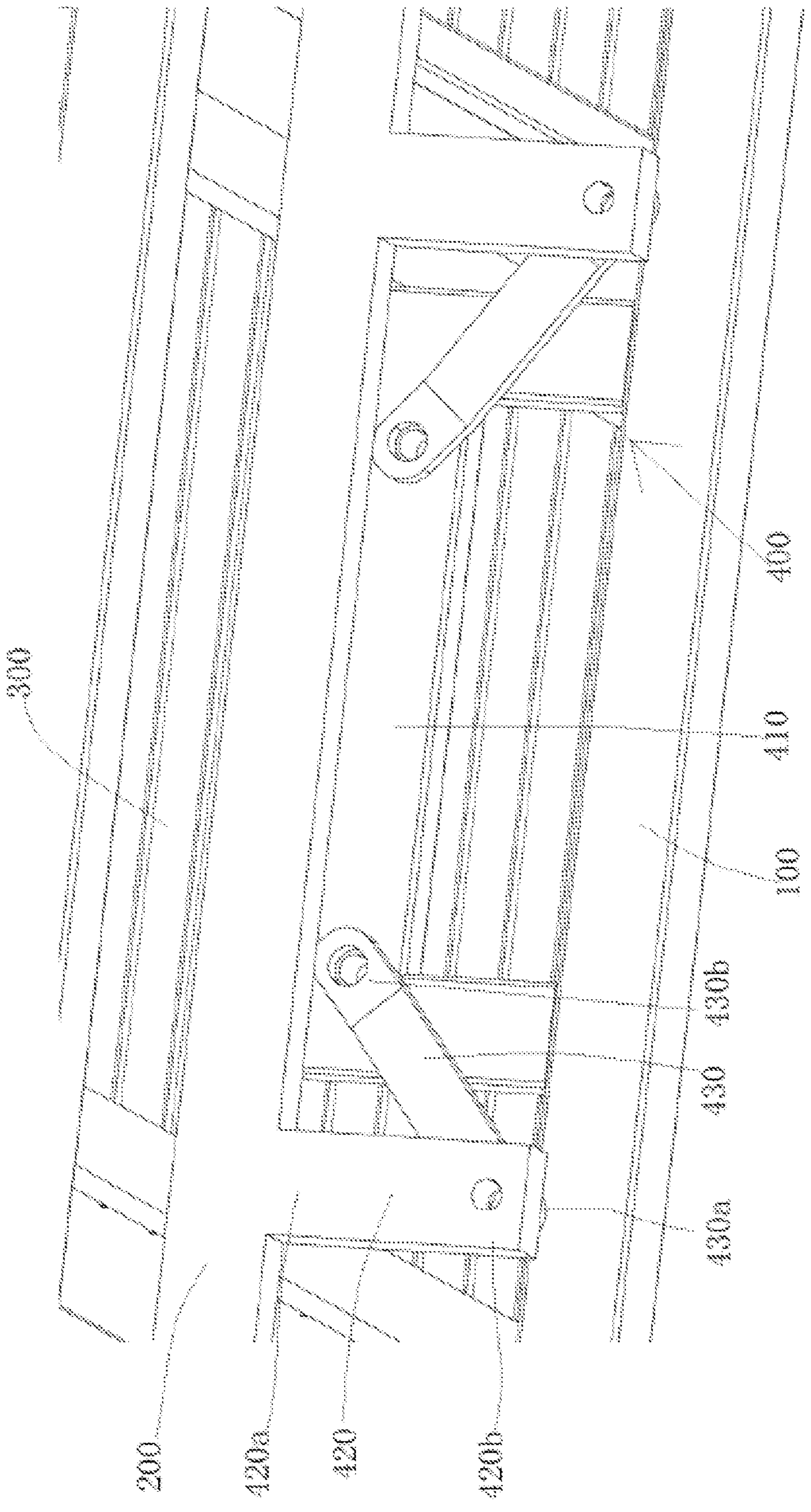
FIG. 4 is an enlarged view of an exemplary swing part of an exemplary electric rocking bed in accordance with preferred embodiments described herein.

As shown in FIG. 4, in preferred embodiments, the swing member 400 includes a support frame 410, a bed frame strut 420, and a swing arm 430. An upper end 420*a* of the bed frame strut 420 is fixed at the bottom of the bed frame 200, and a lower end 420*b* of the bed frame strut 420 is rotationally connected with a second end 430*a* of the swing arm 430. A first end 430*b* of the swing arm 430 is rotationally connected to the support frame 410. Specifically, the lower end 420*b* of the bed frame strut 420 is provided with a circular hole, and the second and first ends 430*a* and 430*b* of the swing arm 430 are respectively provided with a circular hole. The circular hole on the lower end 420*b* of the bed frame strut 420 is rotationally connected with the circular hole of the second end 430*a* of the swing arm 430 through a pin, so that the bed frame strut 420 and the swing arm 430 form a rotational connection relationship, and the circular hole on the first end 430*b* of the swing arm 430 is rotationally connected to the support frame 410 through a pin.

Figure 2:
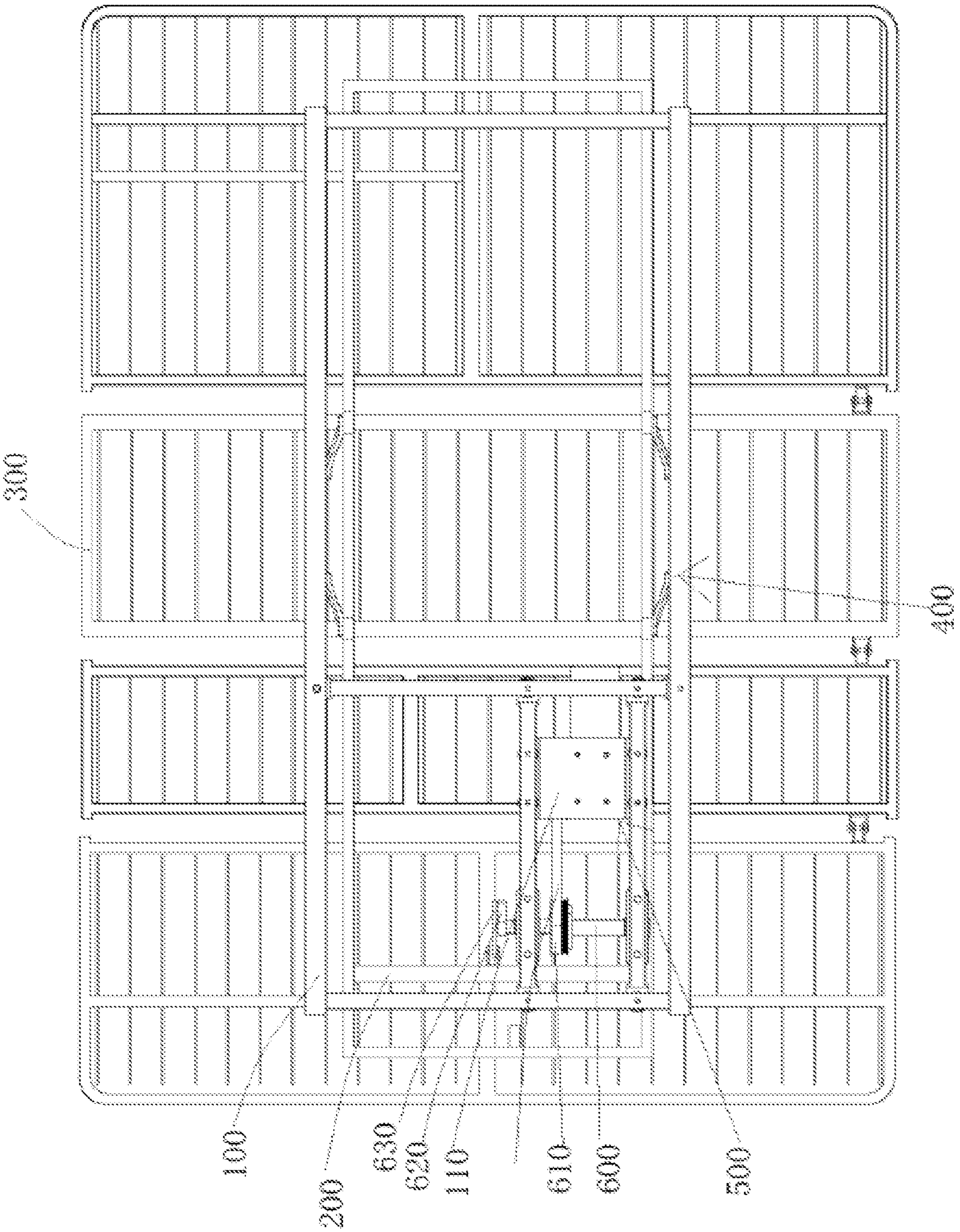
FIG. 2 is a top view of an exemplary electric rocking bed in accordance with preferred embodiments described herein.
Figure 3:
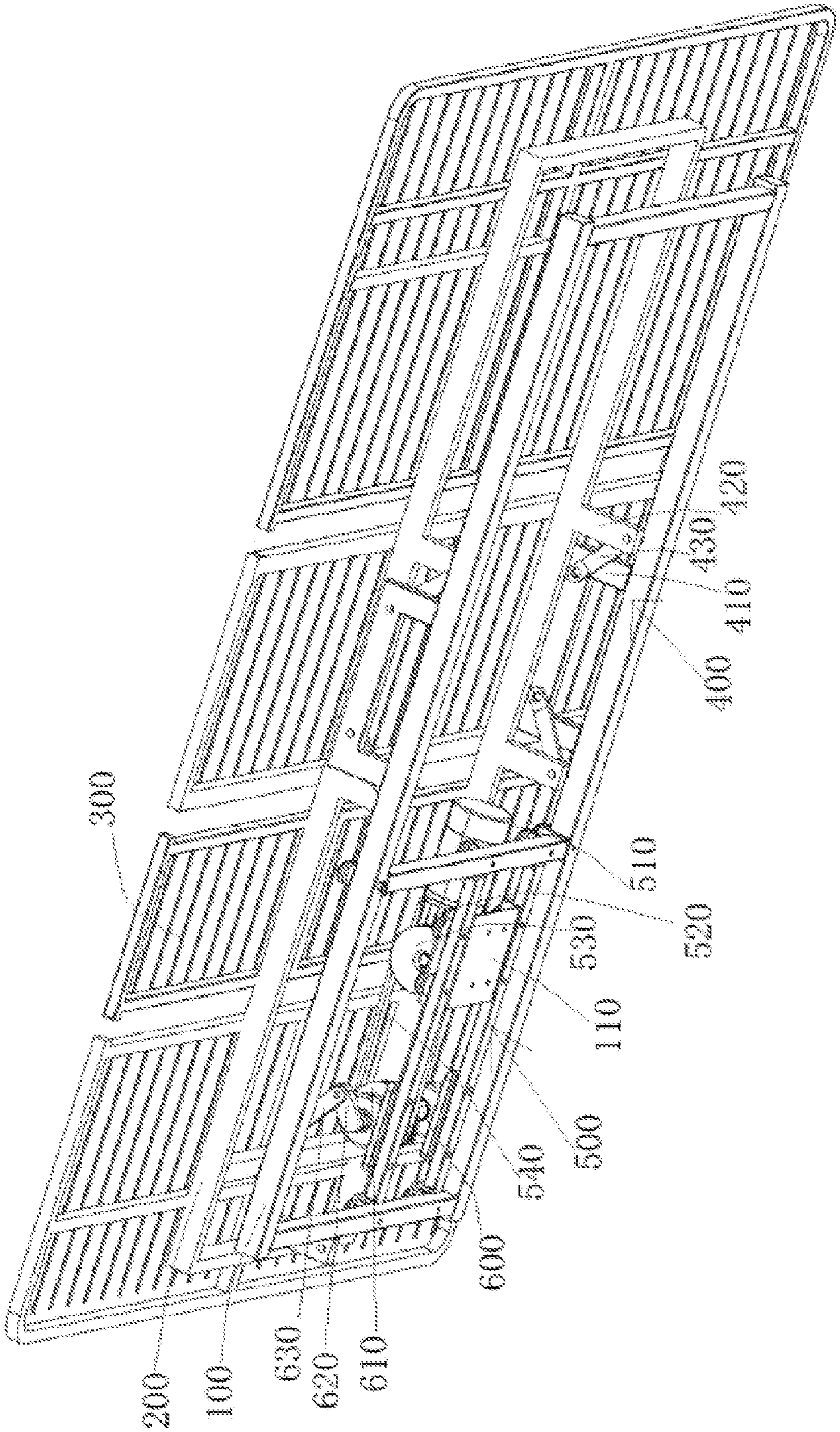
FIG. 3 is a perspective view of an exemplary electric rocking bed in accordance with preferred embodiments described herein.
Figure 5:
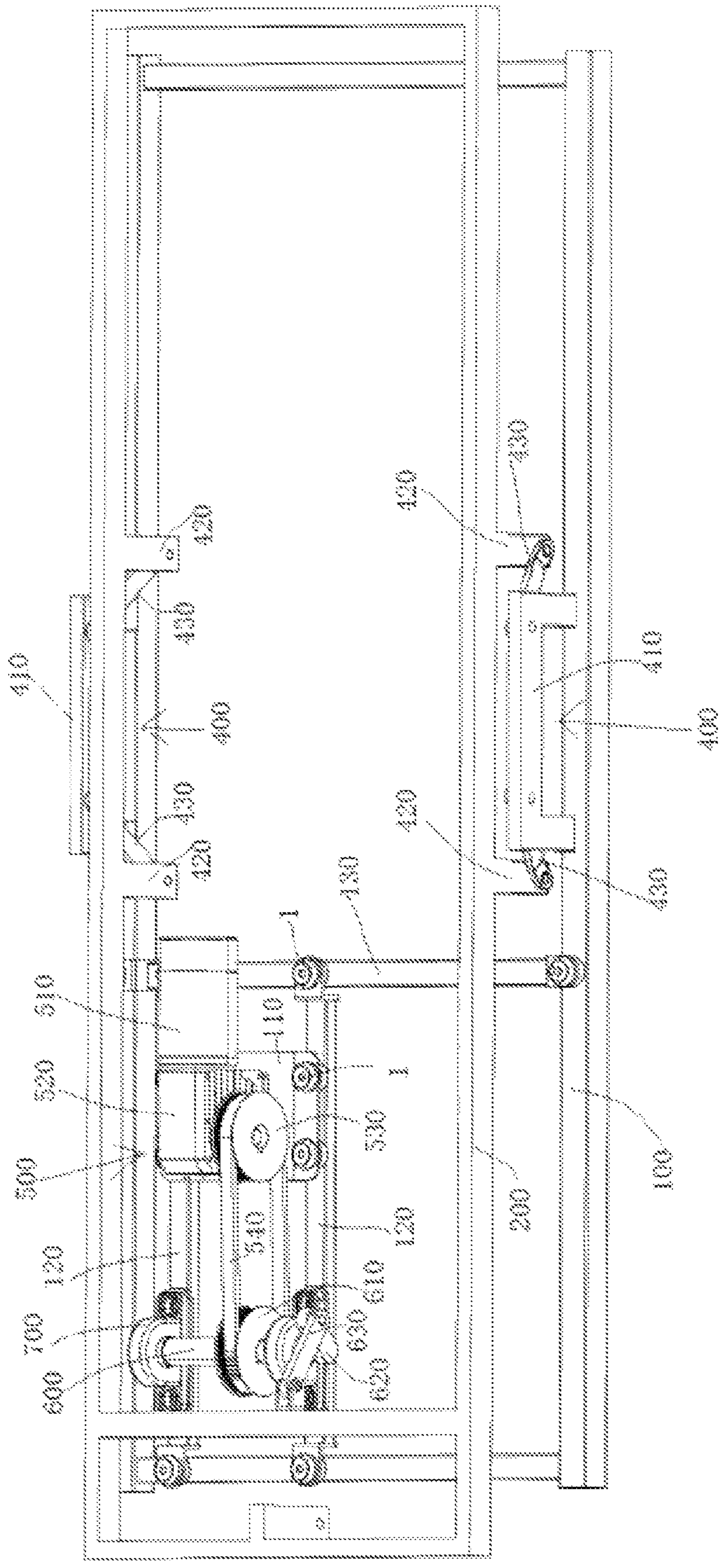
FIG. 5 is a perspective view of an exemplary electric rocking bed without the bed board in accordance with preferred embodiments described herein.
Figure 6:
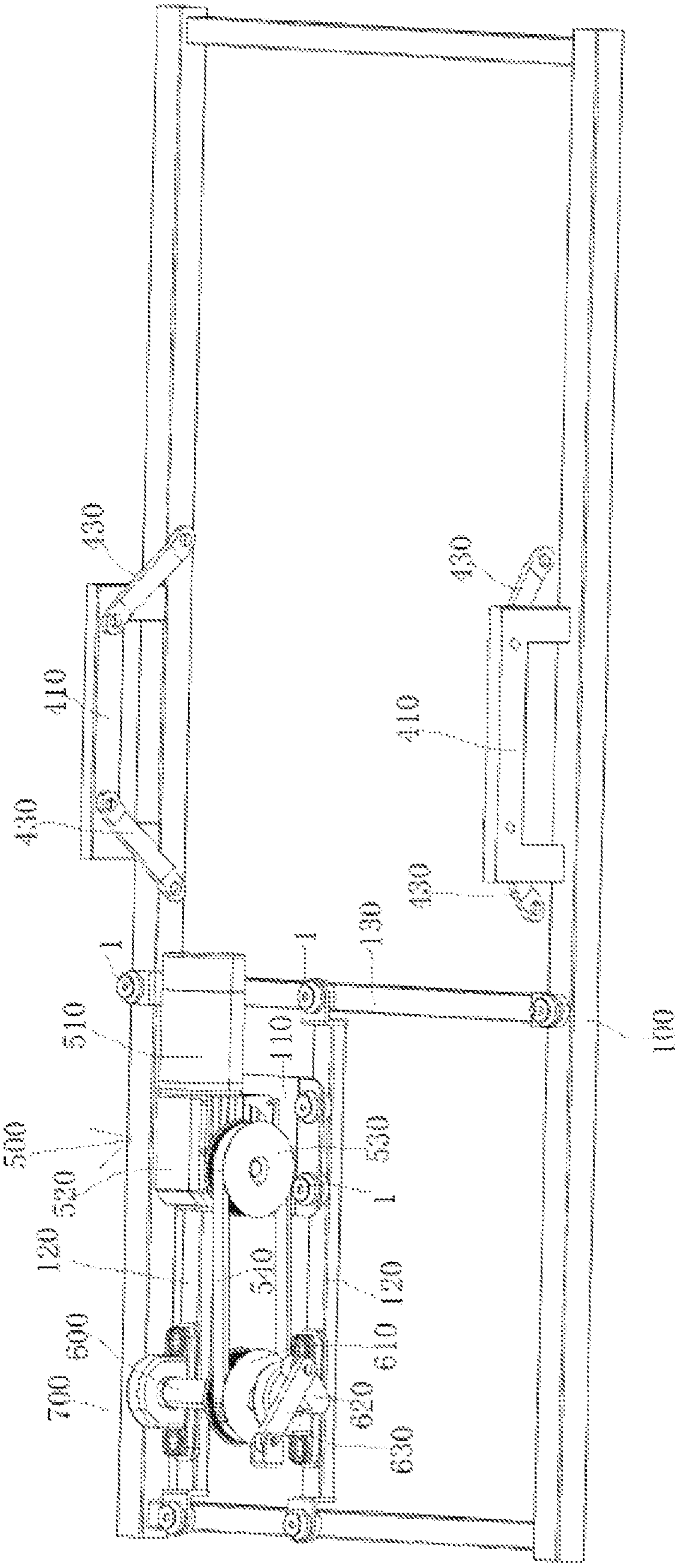
FIG. 6 is a perspective view of an exemplary electric rocking bed without the bed frame in accordance with preferred embodiments described herein.

As shown in FIGS. 2, 3, and 5, a swing part 400 is respectively arranged on both sides of the middle part of the base 100. Specifically, there are two swing parts 400 of the application to be adopted, and the two swing parts 400 are distributed on the left and right sides of the middle of the base 100, so that the base 100 is stressed evenly during the swing process of the bed frame 200, ensuring structural stability.

In the preferred embodiments shown in FIGS. 4 and 5, a swing arm 430 is respectively arranged on both sides of each support frame 410, two swing arms are located on the left and right sides of each support frame 410, and two bed frame struts 420 are arranged at the bottom of the bed frame 200 on the side corresponding to the support frame 410, and the two bed frame struts 420 engage with the two swing arms on that side.

The electric rocking bed described herein makes the thrust of the head and tail of the bed swing evenly through the specially designed driving parts, reduces the impact on the motor and mechanical parts due to the movement of the human body on the bed, and minimizes the noise of the motor and mechanical parts caused by the change of load.

Figure 7:
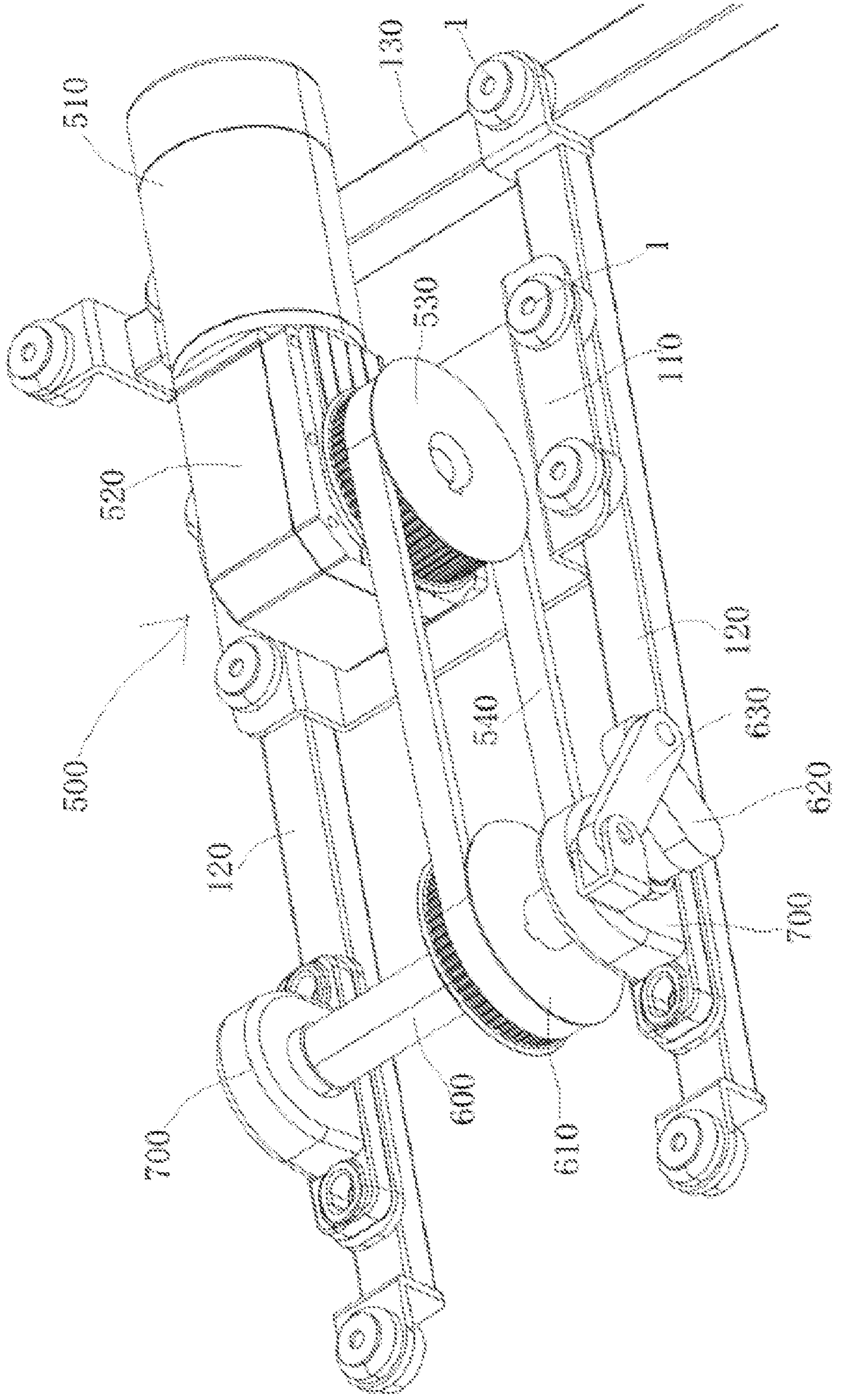
FIG. 7 is an enlarged view of an exemplary driving part of an exemplary electric rocking bed in accordance with preferred embodiments described herein.

As can be seen in FIG. 5 and the enlarged view in FIG. 7, in preferred embodiments the driving part 500 includes a rotating motor 510 fixed on the base 100, the rotating motor 510 is connected with a reducer 520, and the reducer 520 is also connected with a transmission gear 530. The base 100 is provided with a rotating shaft 600, and the rotating shaft 600 is provided with a driven gear 610 connected with the transmission gear 530 through a synchronous belt 540. The rotating shaft 600 is connected with one end of a first rotating arm 620, and the other end of the first rotating arm 620 is connected with one end of a second rotating arm 630. The other end of the second rotating arm 630 is rotationally connected with the bed frame 200, as in FIG. 5. Specifically, one end of the first rotating arm 620 is provided with a connecting hole for the rotating shaft 600 to penetrate into the fixed connection, the other end of the first rotating arm 620 is provided with a circular hole, and one end of the second rotating arm 630 is provided with a through-hole corresponding to the circular hole. Between the other end of the first rotating arm 620 and one end of the second rotating arm 630, a pin penetrates the circular hole and the through-hole to form a rotating connection. The other end of the second rotating arm 630 is rotationally connected with the bed frame 200 through an articulated manner. The electric rocking bed eliminates the click and friction sound caused by the reducer gap through precisely setting the matching parameters of the rotating motor 510 and the reducer 520.

Both ends of the rotating shaft 600 are respectively connected with a bearing assembly 700 on the base 100. One end of the rotating shaft 600 extends out of the bearing assembly 700 and is connected with one end of the first rotating arm 620. There may be two bearing assemblies 700. The two bearing assemblies are matched with both ends of the rotating shaft 600, where one end of the rotating shaft 600 is matched with a bearing assembly 700, and the other end of the rotating shaft 600 extends out of the other bearing assembly 700 through the driven gear 610 and is connected with one end of the first rotating arm 620. This bearing assembly can be constructed according to known principles.

As shown in FIGS. 5 and 7, there is a motor mounting base 110 on the base 100. Both sides of the motor mounting base 110 are respectively provided with a connecting frame 120 connected with the base 100. One end of the two connecting frames is connected with the base 100 through the connecting assembly 1, and the other end of the two connecting frames is connected with the horizontal rail 130 connected to the base 100 through the connecting assembly 1. Both sides of the motor mounting base 110 are detachably connected with the connecting frame 120 through the connecting assembly 1, and two bearing assemblies are placed on the two connecting frames. The connecting assembly 1 is a bolt and a flat nut.

Figure 8:
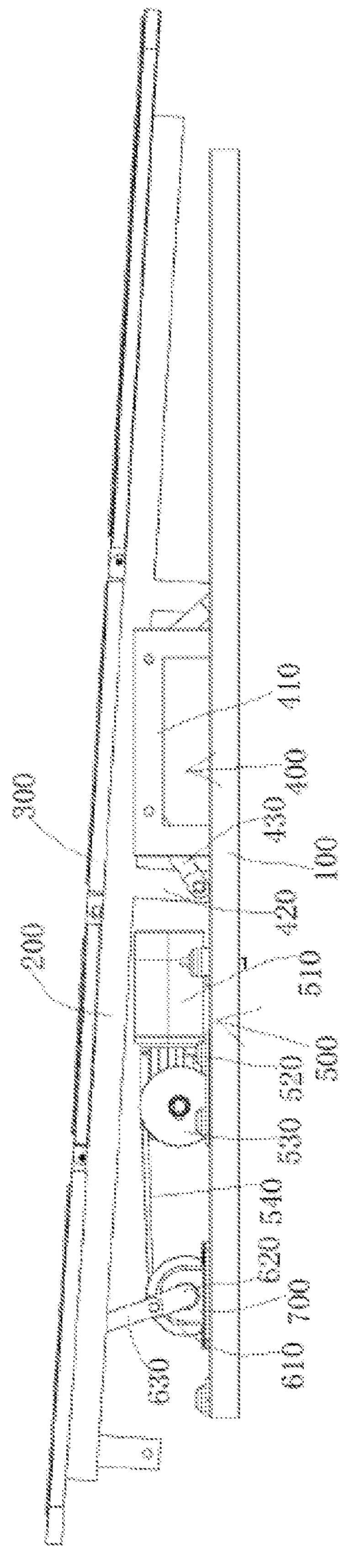
FIG. 8 is a diagram of an exemplary electric rocking bed in a working state in accordance with preferred embodiments described herein.
Figure 9:
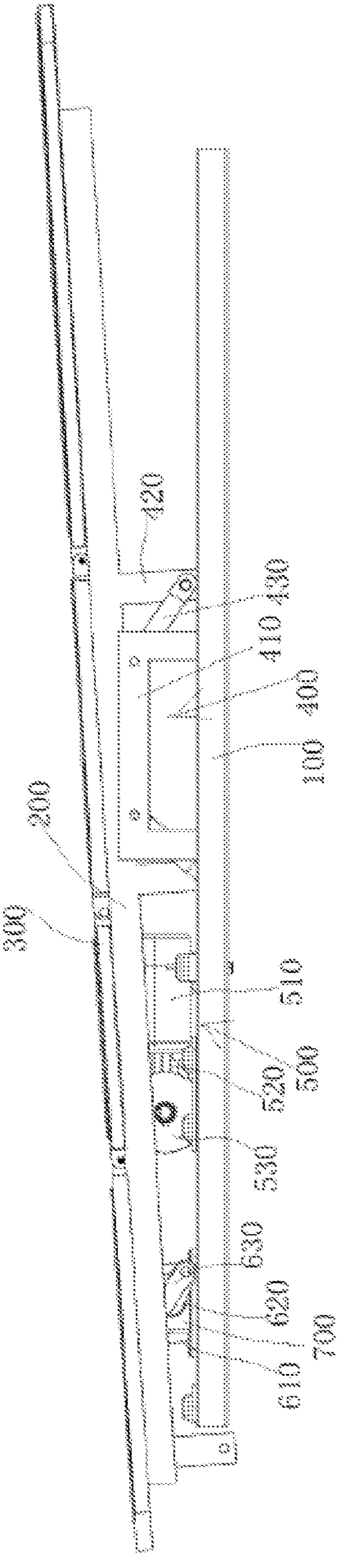
FIG. 9 is a diagram of an exemplary electric rocking bed in a further working state in accordance with preferred embodiments described herein.

As seen in FIGS. 8 and 9, during operation, when the rotating motor 510 of the driving part 500 drives the reducer 520 to work, the reducer 520 drives the transmission gear 530 to rotate, and then drives the driven gear 610 connected with the transmission gear 530 through the synchronous belt 540 to move, and the driven gear 610 drives the rotating shaft 600 to move, and then drives the first rotating arm 620 connected with the rotating shaft 600 to rotate, When the first rotating arm 620 rotates, it drives the second rotating arm 630 to rotate, and then drives the bed frame 200 connected with the second rotating arm 630 to move. At the same time, the movement of the bed frame 200 drives the swinging part 400 to move synchronously, so that the bed frame 200 can rock from head to tail.

Accordingly, preferred embodiments disclosed herein relate to an electric rocking bed that comprises a base, a bed frame positioned above the base, on which a mattress may be placed, at least two swing parts connected to the base and to the bed frame, where the swing parts comprise movable connections and are connected to the bed frame through the movable connections, and a drive part. The bed frame moves relative to the base through movement of the movable connection of the swing parts. The drive part, which is electrically driven, drives the motion of the bed frame relative to the base in a rocking motion. The bed frame may be fixedly or detachedly connected to the base.

In preferred embodiments the bed frame has a top portion and a bottom portion. The top portion is where the mattress would be placed. The bottom of the bed frame may comprise bed frame struts. The swing parts may comprise support frames and swing arms, which serve as the movable connections of the swing parts. The swing arms are rotationally connected to the support frames, which are connected to the base, and the bed frame struts are rotationally connected to the swing arms. In additional embodiments each swing part may comprise one support frame and two swing arms. In further preferred embodiments, the electric rocking bed has a left side and a right side, and two swing parts. Each swing part is preferably positioned centrally or close to the middle of each side of the bed frame, one on the right side and one on the left side. The bed frame of the electric rocking bed may also have two ends, where a sleeper might position his or her head or feet, in addition to the left side and right side. In further preferred embodiments, the drive part of the electric bed connects to the bed frame closer to an end of the bed frame than a central position on the bed frame. The positioning of the drive part, which is connected to the bed frame closer to an end of the bed frame, and the swing parts, connected to the bed frame centrally on sides of the bed frame, sets the fulcrum of the bed on both sides on the middle of the base. This reduces the impact on the motor and mechanical parts due to the posture change of the human body on the bed, ensures structural stability, and reduces stress.

In preferred embodiments the drive part comprises a rotating motor, a reducer, a transmission gear, a rotating shaft, which also comprises a driven gear, a synchronous belt, and a first and second rotating arm. The rotating motor is attached to the base and also to the reducer. The reducer connects to the transmission gear. The synchronous belt runs between and connects the transmission gear to the driven gear of the rotating shaft. The rotating shaft is connected with a first end of the first rotating arm through a pivotal connection. On the other end of the first rotating arm, the first rotating arm is connected to the second rotating arm through a pivotal connection. The other, second end of the second rotating arm is connected to the bed frame through a rotational connection. The rotating motor is electrically driven and, when engaged, engages the reducer, which causes rotation of the transmission gear. The synchronous belt then causes rotation of the rotating shaft. Rotation of the rotating shaft causes movement of the first and second rotating arms, which move the bed frame relative to the base in a rocking motion. The drive part may further comprise bearing assemblies. The rotating shaft may be connected to the bearing assemblies on each end, and one end of the rotating shaft extends out of one of the bearing assemblies to connect with the first end of the first rotating arm. The electric rocking bed may also comprise a motor mounting base, and where the rotating motor is attached to the motor mounting base.

The disclosure and drawings show and describes the basic principle, main features and advantages of the electric rocking bed. Technicians in this industry should understand that this electric rocking bed is not limited by the above embodiments. What is described in the above embodiments and instructions is only to explain the principle of this electric rocking bed. Without departing from the spirit and scope of the electric rocking bed, the electric rocking bed will also have various changes and improvements, which fall within the scope of the current disclosure.

What is claimed is:

1. An electric rocking bed, comprising:

a base;

a bed frame positioned above the base, wherein the bed frame has two sides and two ends;

at least two swing parts connected to the base and to the bed frame, wherein the swing parts comprise movable connections, wherein the swing parts are connected to the bed frame through the movable connections on each side of the bed frame, wherein each movable connection acts as a fulcrum on each side of the bed frame through which the bed frame moves relative to the base, and wherein the bed frame moves in a swinging motion from end to end relative to the base through movement of the movable connection of the swing parts; and a drive part connected to the base and to the bed frame, wherein the drive part moves the bed frame relative to the base, wherein the drive part comprises a rotating motor, a reducer, a transmission gear, a rotating shaft comprising a driven gear, a synchronous belt, and a first and second rotating arm, wherein the rotating motor is attached to the base and to the reducer, wherein the reducer is connected to the transmission gear, wherein the synchronous belt connects the transmission gear to the driven gear of the rotating shaft, wherein the rotating shaft is connected with a first end of the first rotating arm through a pivotal connection, wherein the first and second rotating arms are connected to each other through a pivotal connection, wherein a second end of the second rotating arm is connected to the bed frame through a rotational connection, and wherein rotation of the rotating shaft causes movement of the first and second rotating arms to move the bed frame relative to the base.

2. The electric rocking bed of claim 1, wherein the bed frame has a top portion and a bottom portion, wherein the bottom portion of the bed frame comprises bed frame struts, wherein the swing parts further comprise support frames, wherein the movable connections of the swing parts comprise swing arms, wherein the swing arms are rotationally connected to the support frames, wherein the support frames are connected to the base, and wherein the bed frame struts are rotationally connected to the swing arms.

3. The electric rocking bed of claim 2, wherein each swing part comprises a support frame and two swing arms.

4. The electric rocking bed of claim 1, wherein the electric rocking bed comprises two swing parts, wherein the bed frame has a left side and a right side, and wherein the swing parts are positioned centrally on the right side and the left side of the bed frame.

5. The electric rocking bed of claim 1, wherein the base further comprises a motor mounting base, and wherein the rotating motor is attached to the motor mounting base.

6. The electric rocking bed of claim 1, wherein the drive part further comprises bearing assemblies, wherein the rotating shaft is connected to the bearing assemblies, and wherein the rotating shaft extends out of a bearing assembly to connect with the first end of the first rotating arm.

7. An electric rocking bed, comprising:

a base;

a bed frame positioned above the base;

at least two swing parts connected to the base and to the bed frame, wherein the swing parts comprise movable connections, wherein the swing parts are connected to the bed frame through the movable connections, and wherein the bed frame moves relative to the base through movement of the movable connection of the swing parts; and a drive part connected to the base and to the bed frame, wherein the drive part moves the bed frame relative to the base in a rocking motion, wherein the drive part comprises a rotating motor, a reducer, a transmission gear, a rotating shaft comprising a driven gear, a synchronous belt, and a first and second rotating arm, wherein the rotating motor is attached to the base and to the reducer, wherein the reducer is connected to the transmission gear, wherein the synchronous belt connects the transmission gear to the driven gear of the rotating shaft, wherein the rotating shaft is connected with a first end of the first rotating arm through a pivotal connection, wherein the first and second rotating arms are connected to each other through a pivotal connection, wherein a second end of the second rotating arm is connected to the bed frame through a rotational connection, and wherein rotation of the rotating shaft causes movement of the first and second rotating arms to move the bed frame relative to the base.

8. The electric rocking bed of claim 7, wherein the base further comprises a motor mounting base, and wherein the rotating motor is attached to the motor mounting base.

9. The electric rocking bed of claim 7, wherein the drive part further comprises bearing assemblies, wherein the rotating shaft is connected to the bearing assemblies, and wherein the rotating shaft extends out of a bearing assembly to connect with the first end of the first rotating arm.

* * * * *